US00PP28629P2

(12) United States Plant Patent
Schelble et al.

(10) Patent No.: US PP28,629 P2
(45) Date of Patent: Nov. 14, 2017

(54) ***LITHODORA* PLANT NAMED 'LITGS'**

(50) Latin Name: *Lithodora diffusa*
Varietal Denomination: LITGS

(71) Applicants: Judith Ann Schelble, Yelm, WA (US); Timothy Clark Schelble, Yelm, WA (US)

(72) Inventors: Judith Ann Schelble, Yelm, WA (US); Timothy Clark Schelble, Yelm, WA (US)

( * ) Notice: Subject to any disclaimer, the term of this patent is extended or adjusted under 35 U.S.C. 154(b) by 0 days.

(21) Appl. No.: 15/330,217

(22) Filed: Aug. 23, 2016

(51) Int. Cl.
*A01H 5/02* (2006.01)

(52) U.S. Cl.
USPC ..... Plt./263.1

(58) Field of Classification Search
USPC ..... Plt./263.1, 226
CPC ..... A01H 5/02; A01H 5/00
See application file for complete search history.

*Primary Examiner* — June Hwu
(74) *Attorney, Agent, or Firm* — Klarquist Sparkman, LLP

(57) ABSTRACT

A new and distinct form of *Lithodora* plant characterized by yellow to lime foliage that maintains its color all summer, flowers, a low spreading habit, excellent dense branching with flower clusters at the end of every branch, excellent vigor, and good garden performance.

1 Drawing Sheet

Botanical denomination: *Lithodora diffusa.*
Variety designation: 'LITGS'.

BACKGROUND OF THE INVENTION

The present invention relates to a new and distinct cultivar of *Lithodora*, given the name, 'LITGS'. *Lithodora* is in the family Boraginaceae. This new cultivar was found in a nursery in Yelm, Wash. as a naturally occurring branch mutation of *Lithodora diffusa* 'Grace Ward', an unpatented plant.

The new cultivar is unique with its yellow to lime leaf color. There are no others with yellow to lime leaves on the market known to the inventor. In addition it exhibits the following characteristics:

1. a low, spreading habit,
2. excellent dense branching with flower clusters at end of every branch,
3. maintains the yellow to lime foliage color all summer,
4. excellent vigor, and
5. good garden performance.

Compared to the mother plant, *Lithodora diffusa* 'Grace Ward' the new cultivar yellow to lime colored leaves rather than green leaves.

The new variety has been reproduced only by asexual propagation (stem cuttings and micropropagation using tips). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a nine-month-old *Lithodora* 'LITGS' in bloom growing in the trial field in May in Canby, Oreg.

FIG. 2 shows the nine-month-old plants growing in full sun in July in Chiba, Japan.

DETAILED PLANT DESCRIPTION

The following is a detailed description of the new *Lithodora* cultivar based on observations of one-year-old specimens in May grown outside in the ground in the trial beds in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5$^{th}$ edition, 2007.

Plant:

*Form.*—Spreading.
*Type.*—Evergreen, mat forming subshrub/perennial/groundcover.
*Cold hardiness.*—USDA Zone 5a-8.
*Size.*—Grows to 55 cm wide and 9 cm tall to the top of the foliage.
*Vigor.*—Excellent.
*Branching.*—Extremely well-branched.
*Stem.*—Grows to 30 mm long, pubescent, internodes range from 3 mm to 7 mm long, Yellow Green 147C; older woody stems grow to 3 mm wide, Brown 200A.
*Roots.*—Fibrous, freely branching, plants root easily from stem tip cuttings.

Leaf:

*Type.*—Simple.
*Arrangement.*—Alternate.
*Blade size.*—Grow to 14 mm long and 4 mm wide.
*Petiole description.*—Sessile.
*Shape.*—Linear lanceolate.
*Venation.*—Pinnate.
*Margins.*—Revolute.
*Apex.*—Acute.

*Base*.—Truncate.

*Surface texture*.—Pubescent of both sides.

*Leaf color*.—Top and bottom side spring, summer, fall and winter Yellow 11A including vein, darkening to Yellow Green 144A where shaded.

Inflorescence:

*Type*.—Terminal cyme.

*Number of flowers*.—3 to 6 per cyme.

*Size of inflorescence*.—Spreads 3 cm wide and 1.5 cm deep.

*Peduncle*.—None.

*Pedicel*.—None.

*Bloom period*.—Middle of April to middle of May in Canby, Oreg.

Flower bud:

*Size*.—11 mm long and 3 mm wide at the widest point prior to opening.

*Description*.—Tubular.

*Surface texture*.—Pubescent.

*Color*.—Purple N79D with Violet Blue 90C on top.

Flower:

*Type*.—Regular.

*Shape*.—Rotate to salverform.

*Corolla description*.—13 mm wide and 13 mm deep, pubescent inside and outside; tube 10 mm long and 2 mm to 2.5 mm wide, 5 lobes, each lobe 6 mm long and 5 mm wide (connecting on the bottom 2 mm), oblong, margins entire, tips obtuse, lobes top side Blue 101B with the midrib Violet Blue 98A, bottom side Violet Blue 98A; tube Purple N79C.

*Calyx description*.—campanulate, 2 mm wide and 6 mm deep, 5-lobed, lobes linear lanceolate, tips acuminate, margins entire, both sides Yellow 11A and pubescent.

*Pistil description*.—1, 11 mm long, ovary 4 lobed and about 1 mm long and 1 mm wide, Yellow Green 145C, style 10 mm long, White 155A, stigma White 155A.

*Stamen description*.—5, filaments 5 mm long and Greyed Purple 187C, anthers 1 mm long and Greyed Yellow 158A, pollen Greyed Yellow 158D.

*Fragrance*.—None.

*Lastingness*.—A cyme blooms for about 2 weeks on the plant.

Seed: Nutlets, none seen.

Pests and diseases: *Lithodora* have no major pests or disease problems. This plant has shown no special disease or pest resistance in Canby, Oreg.

We claim:

1. A new and distinct form of *Lithodora* plant substantially as shown and described.

* * * * *

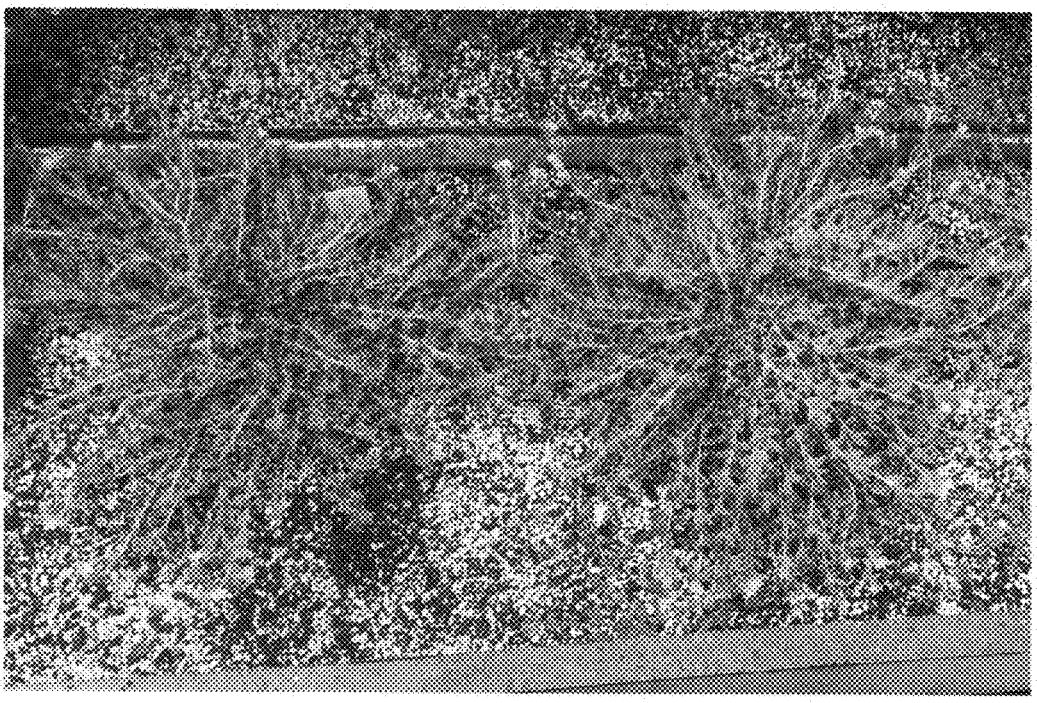

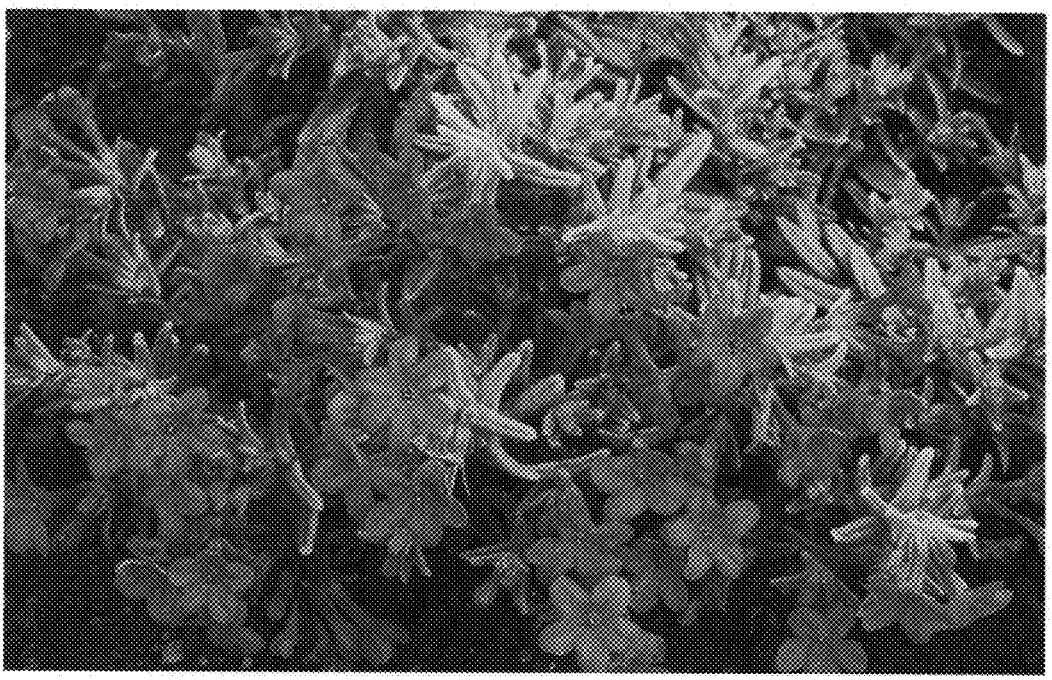
FIG. 1 above, FIG. 2 below